United States Patent [19]

Fujiwara et al.

[11] Patent Number: 4,778,902

[45] Date of Patent: Oct. 18, 1988

[54] METHOD OF PURIFYING L-ASCORBIC ACID

[75] Inventors: Yoshitaka Fujiwara; Tetsuji Kaizu; Masami Shinohara, all of Yamaguchi, Japan

[73] Assignee: Takeda Chemical Industries, Ltd., Osaka, Japan

[21] Appl. No.: 880,821

[22] Filed: Jul. 1, 1986

[30] Foreign Application Priority Data

Jul. 5, 1985 [JP] Japan .................. 60-148921

[51] Int. Cl.$^4$ ............................ C07D 307/62
[52] U.S. Cl. .................................. 549/315
[58] Field of Search ........................ 549/315

[56] References Cited

U.S. PATENT DOCUMENTS 4,233,202  11/1980  Berger et al. ................ 549/542

FOREIGN PATENT DOCUMENTS 53-98955  8/1978  Japan .

OTHER PUBLICATIONS

Ikuo Abe et al, Chemical Abstracts 85:51333y.
M. Takashio et al, Chemical Abstracts 90:56246k.
M. Layard et al, Chemical Abstracts 103:110485q; Journal de Chimie Physique (1985), vol. 82(4), pp. 415–419.
English Translation of Japan 53/98,955.

*Primary Examiner*—Norma S. Milestone
*Attorney, Agent, or Firm*—Wegner & Bretschneider

[57] ABSTRACT

A method of purifying L-ascorbic acid which comprises: bringing an acidic aqueous solution of L-ascorbic acid which contains a cationic surfactant into contact with active carbon activated by chemicals.

The method is in particular useful for removing a cationic surfactant from a reaction mixture of diacetone-2-keto-L-gulonic acid or 2-keto-L-gulonic acid with a mineral acid in the presence of an inert solvent and a cationic surfactant, to produce L-ascorbic acid.

5 Claims, No Drawings

METHOD OF PURIFYING L-ASCORBIC ACID

This invention relates to a method for purifying L-ascorbic acid, and in particular, to a method of purifying L-ascorbic acid by removing therefrom a cationic surfactant contained in L-ascorbic acid produced from diacetone-2-keto-L-gulonic acid or 2-keto-L-gulonic acid in the presence of a cationic surfactant.

A process is already known for producing L-ascorbic acid in which diacetone-2-keto-L-gulonic acid or 2-keto-L-gulonic acid is reacted with a mineral acid in the presence of a solvent inert to the resulting L-ascorbic acid, such as an aromatic hydrocarbon, and a cationic surfactant, and then the resultant L-ascorbic acid which crystallizes out is separated from the reaction mixture usually by filtration, as disclosed in Japanese Patent Publication No. 48-15931.

This process provides L-ascorbic acid in high yields, and the cationic surfactant is removed therefrom in the purification step of L-ascorbic acid. Although it is already known that the treatment of an aqueous solution of L-ascorbic acid which contains a small amount of iron effectively removes the iron from the solution, as disclosed in Japanese Patent Disclosure No. 53-98955, but no method has been hiterto known which makes it possible to industrially and advantageously remove the cationic surfactant from the resultant L-ascorbic acid.

An object of this invention is therefore to provide a method of purifying L-ascorbic acid, and in particular, to provide a method of removing a cationic surfactant contained in L-ascorbic acid.

A method of purifying L-ascorbic acid of the invention comprises: bringing an acidic aqueous solution of L-ascorbic acid which contains a cationic surfactant into contact with active carbon activated by chemicals.

The method of the invention is applicable to any aqueous solution of L-ascorbic acid which contains a cationic surfactant, however, the method is in particular useful for removing a cationic surfactant from a reaction mixture obtained by the process for producing L-ascorbic acid, as mentioned hereinbefore. Such a reaction mixture may be obtained by reacting diacetone-2-keto-L-gulonic acid or 2-keto-L-gulonic acid with a mineral acid in the presence of an inert solvent and a cationic surfactant. The method of the invention is industrially and advantageously utilizable for the removal of a cationic surfactant from such a reaction mixture.

As an aspect of the invention, the reaction mixture as above is treated as follows before the contact with active carbon. Since the reaction mixture contains L-ascorbic acid precipitate, water is first added to the reaction mixture to dissolve the precipitate, an alkali is added to the mixture in amounts equivalent to the amount of the mineral acid in the mixture to neutralize the mineral acid, and then the aqueous layer is separated from the mixture. The thus obtained aqueous solution contains L-ascorbic acid together with a cationic surfactant and by-products such as acetone, and is acidic, usually at a pH of 1.5 to 2.5.

The aqueous solution may then be contacted with active carbon activated by chemicals, which being hereinafter referred to as chemicals-activated carbon. However, it is preferred that the solution is distilled to remove the acetone and then the resultant insoluble substance is removed therefrom by filtration, to provide an aqueous solution which usually contains L-ascorbic acid in amounts of 10–30% (W/V) and a cationic surfactant in amounts of 50–5000 ppm. In the method of the invention, it is preferred to put this solution into contact with chemicals-activated carbon.

In the prior art, the resultant precipitate of L-ascorbic acid is separated by filtration and purified by washing. However, since the resultant L-ascorbic acid in the reaction mixture is a muddy substance composed of very fine precipitates, it is difficult to fully remove the solvent therefrom, but also the resultant cake is readily cracked to make the washing of the cake incomplete. Further, the reaction mixture as obained is corrosive to filtration apparatus since the reaction mixture contains a mineral acid as well as an organic solvent, so that it is difficult to choose a filtration apparatus which stands both the mineral acid and organic solvent.

The method of the invention is superior to the above prior method of purification of L-ascorbic acid. According to the invention, the precipitate of L-ascorbic acid in the reaction mixture is dissolved by adding water to the reaction mixture, and an alkali to neutralize the mineral acid therein, and then the aqueous layer is separated from the inert solvent. The resultant aqueous solution therefore contains a less amount of impurities than the initial reaction mixture is obtained, and the solution, preferably after further removal of the by-produced acetone, for example, by distillation in vacuo, is put into contact with chemicals-activated carbon, to remove effectively the cationic surfactant.

The cationic surfactant contained in the aqueous solution of L-ascorbic acid includes, for example, quaternary ammonium salts such as stearyltrimethylammonium chloride, alkylamines such as stearylamine, distearylamine, dimethylstearylamine, stearylpropylenediamine or stearylpropylenediamine dioleate, alkylpyridinium salts such as an alkylpyridinium chloride.

The aqueous solution containing such a cationic surfactant is made contact with chemicals-activated carbon in an acidic condition usually at a pH of not more than about 5 in the invention.

According to the invention, it is necessary to use chemicals-activated carbon to remove effectively a cationic surfactant from an aqueous solution containing the cationic surfactant and L-ascorbic acid. The active carbon may be powder or granular. Active carbons activated by gas, for instance, by steam, are ineffective for removing a cationic surfactant from L-ascorbic acid.

The chemicals-activated carbon usable in the invention is not specifically limited, but preferably has pores of not more than 15 μm in diameter in pore volume not less than 0.7 cc/g, and pores of not more than 300 Angstroms in diameter in pore volume not less than 0.4 cc/g, wherein the pores of not more than 300 Angstroms in diameter have an average pore diameter of not less than 17 Angstroms. As well known, the pore volume of pores of not more than 15 μm in diameter may be determined by mercury porosimetry, nitrogen adsorption method, etc, as described in "Adsorption," pp. 95–113 (1967), Kyoritsu Shuppan K.K. The pore volume of pores of not more than 300 Angstrom in diameter may be determined also by the nitrogen adsorption method. The average pore diameter (d) of pores of not more than 300 Angstrom in diameter is calculated from the equation: $d = 4v/s$ wherein v is the pore volume of pores of not more than 300 Angstrom in diameter on the asumption that they are cylindrical in the form, and s is the specific surface area calculated from the BET adsorption isotherm of nitrogen gas. However, the above pore properties are only illustrative, and are not critical in the invention.

The chemicals-activated carbon as specified as above may be produced, as is well known, by immersing wooden material such as wood, sawdust, or coconut shell in chemicals such as zinc chloride, phosphoric acid or calcium chloride, baking the thus treated material at temperatures of about 600°–700° C., and removing the chemical used by washing the baked material with an acid, e.g., hydrochloric acid. Among these active carbons, however, is most preferred an active carbon produced by zinc chloride-activation.

The chemicals-activated carbon may be powder or granular, and the latter is preferred. More specifically, granular active carbon is most preferred which contains granules of 8–250 mesh (according to JIS) in amounts of not less than 90%. These chemicals-activated carbon are availble as commercial products, such as "Special Shirasagi" and "Strong Shirasagi" for chromatography by Takeda Chemical Industries, Ltd.

Any method is adoptable to bring the aqueous solution of L-ascorbic acid which contains a cationic surfactant into contact with the chemicals-activated carbon. For instance, the solution may be simply mixed with the active carbon, followed by filtration to remove the active carbon, or the solution may be put into contact with the active carbon by the use of fixed bed, moving bed or fluidized bed of the active carbon. The contact of the solution with the fixed bed active carbon is industrially advantageous, in which the solution is passed through a column having the active carbon filled therein upwardly or downwardly, since the fixed bed contact is easy in operation and high in adsorption efficiency of cationic surfactant to the active carbon. The cationic surfactant is adsorbed onto the active carbon and separated from the solution while L-ascorbic acid is contained in the resultant effluent.

The amount of the chemicals-activated carbon used is dependent upon the method in which the solution is made contact with the carbon and adsorption utility of the carbon as well. However, when the fixed bed active carbon is adopted, it is preferable to use the active carbon in amounts of 2–10% by weight based on L-ascorbic acid in the solution. The used active carbon may be regenerated by a known method, for example, by washing the carbon with an acid, alkali or an organic solvent.

After the removal of the cationic surfactant, the aqueous solution of L-ascorbic acid may be treated in any conventional manner to provide purified L-ascorbic acid. Usually the solution is concentrated to crystallize out L-ascorbic acid.

The invention will be understood more readily with reference to the following examples; however, these examples are intended to illustrate the invention only and are not construed as limitation to the invention.

EXAMPLE 1

A cationic surfactant, i.e., a primary amine, secondary amine, tertiary amine or quaternary amine, was added in amounts of 300 ppm to a 20% (W/V) solution of L-ascorbic acid. The resultant aqueous solution had a pH of 2.3. An amount of 0.5 g of an active carbon shown in Table 1 was added to 100 ml of the solution, which was stirred at room temperature for 30 minutes, and then the active carbon was removed by filtration. The filtrate was shaken to determine the degree of foaming by the naked eye. The result is shown in Table 1, in which the degree of foaming is graded to 1 to 5.

TABLE 1

| Cationic Surfactant | Active carbon activated by | | |
|---|---|---|---|
| | steam[1] | zinc chloride[2] | Control[3] |
| Stearylamine | 4 | 1 | 5 |
| Distearylamine | 4 | 1 | 5 |
| Dimethylstearylamine | 4 | 1 | 5 |
| Stearyltrimethylammonium chloride | 4 | 1 | 5 |

Note: The grade was taken 5 to the control, and 1 when substantially no foaming was observed.
[1]"Shirasagi A" by Takeda Chemical Industries, Ltd.
[2]"Strong Shirasagi" by Takeda Chemical Industries, Ltd.
[3]Without treating by active carbon.

As apparent from the result, the solution, when being treated with active carbon activated by zinc chloride, was found substantially not to foam, illustrating that the cationic surfactant in the solution was effectively removed by the active carbon activated by zinc chloride, whereas active carbon activated by steam was found almost ineffective for removing the cationic surfactant from the solution.

EXAMPLE 2

To 100 g of diacetone-2-keto-L-gulonic acid hydrate was added 300 ml of benzene, 0.1 g of stearylpropylenediamine as a cationic surfactant and 10 ml of conc. hydrochloric acid, and the resultant mixture was heated at a temperature of 65° C. for 5 hours. The reaction mixture was then cooled and 220 ml of water was added thereto to dissolve the resultant L-ascorbic acid therein.

A 30% by weight aqueous solution of sodium hydroxide was added to the mixture in amounts equivalent to the amount of the hydrochloric acid in the mixture, and then an aqueous layer was separated from the mixture. An amount of about 300 ml of the aqueous solution was distilled in vacuo to remove acetone therefrom to provide 210 ml of an aqueous solution of L-ascorbic acid containing the cationic surfactant. The solution had a pH of 2.0.

The solution was divided to two, and to each 105 ml of the solution was added 1.0 g of active carbon powder as shown in Table 2, the mixture was stirred at room temperature for 30 minutes, and then the active carbon was removed by filtration. The each filtrate was found to contain 28.3 g of L-ascorbic acid (94% yield) and the cationic surfactant in amounts as shown in Table 2.

TABLE 2

| Active carbon | Content of surfactant (ppm)[3] | |
|---|---|---|
| | Initial | After treatment |
| Activated by steam[1] | 305 | 180 |
| Activated by zinc chloride[2] | 305 | 10 |

[1]"Shirasagi A" by Takeda Chemical Industries, Ltd.
[2]"Strong Shirasagi" by Takeda Chemical Industries, Ltd. No foaming was observed.
[3]By Eosin coloring-chloroform extraction followed by colorimetric determination.

EXAMPLE 3

To 300 g of diacetone-2-keto-L-gulonic acid hydrate was added 900 ml of toluene, 0.9 g of stearylpropylenediamine dioleate as a cationic surfactant and 39 ml of conc. hydrochloric acid, and the resultant mixture was heated at 65° C. for 5 hours. The reaction mixture was then cooled and 660 ml of water was added thereto to dissolve the resultant L-ascorbic acid therein.

A 30% by weight aqueous solution of sodium hydroxide was added to the mixture in amounts equivalent to the amount of the hydrochloric acid in the mixture, and then an aqueous layer was separated from the mixture. An amount of about 910 ml of the aqueous solution was distilled in vacuo to remove acetone therefrom and then filtered to remove the resultant insoluble substance to provide 650 ml of a dark brown aqueous solution of L-ascorbic acid containing the cationic surfactant in amounts of 520 ppm.

The solution was passed through a column of 1.0 cm in inner diameter and 76 cm in height having 60 ml of the same active carbon activated by zinc chloride as before in a rate of space velocity of 2. The resultant solution was substantially colorless and no surfactant was detected in the solution by the same test as before. The solution was also found to contain 168.3 g of L-ascorbic acid (93% yield).

What is claimed is:

1. A method of purifying L-ascorbic acid which comprises:
   (a) preparing an acidic aqueous solution of L-ascorbic acid which contains an alkylamine and has a pH of not more than 5 from a reaction mixture of a reaction of diacetone-2-keto-L-gulonic acid or 2-keto-L-gulonic acid with a mineral acid in the presence of the alkylamine and a solvent inert to the resulting L-ascorbic acid, the reaction mixture containing the precipitated L-ascorbic acid, the alkylamine, water, the solvent and acetone as a by-product, by adding water to the reaction mixture sufficient to dissolve the precipitated L-ascorbic acid, adding an alkali in amounts equivalent to the amount of the mineral acid in the mixture to neutralize the mineral acid, separating the resultant aqueous layer from the mixture, and removing the acetone from the solution; and
   (b) bringing the acidic aqueous solution of L-ascorbic acid which contains an alkylamine into contact with active carbon activated by a member of the group consisting of zinc chloride, phosphoric acid and calcium chloride.

2. The method as claimed in claim 1 wherein the active carbon is active carbon activated by zinc chloride.

3. The method as claimed in claim 1, wherein the aqueous solution contains L-ascorbic acid therein in amounts of 10–30% (W/V).

4. The method as claimed in claim 1, wherein the aqueous solution contains the alkylamine therein in amounts of 50–5000 ppm.

5. THe method as claimed in claim 1, wherein the aqueous solution has a pH of 1.5–2.5.

* * * * *